United States Patent [19]
Shirley

[11] 4,342,518
[45] Aug. 3, 1982

[54] SUBSEAFLOOR ENVIRONMENTAL SIMULATOR

[75] Inventor: Donald J. Shirley, Leander, Tex.

[73] Assignee: The United States of America as represented by the Secretary of the Navy, Washington, D.C.

[21] Appl. No.: 211,600

[22] Filed: Dec. 1, 1980

[51] Int. Cl.³ .................... G01N 25/18; G01N 29/00
[52] U.S. Cl. ........................................ 374/44; 73/594; 73/597
[58] Field of Search ............... 73/432 SP, 15 A, 15.4, 73/597, 599, 594, 37, 38

[56] References Cited

U.S. PATENT DOCUMENTS

| | | | |
|---|---|---|---|
| 3,115,772 | 12/1963 | O'Keefe et al. | 73/37 |
| 3,817,109 | 6/1974 | Audet et al. | 73/15 A |
| 3,934,455 | 1/1976 | Harrisberger | 73/38 |
| 4,038,629 | 7/1977 | Van Der Burgt et al. | 73/597 |
| 4,304,122 | 12/1981 | Tentor | 73/432 SD |

*Primary Examiner*—S. Clement Swisher
*Attorney, Agent, or Firm*—R. F. Beers; Francis I. Gray

[57] ABSTRACT

A subseafloor simulator for measuring acoustical and other physical properties of sediments at temperatures and pressures that simulate the real ocean environment. A pressure chamber has a porous piston to exert a required overburden pressure to simulate the weight of the mineral grains. An inlet port allows the fluid pressure inside the pressure chamber to be independently controlled. Acoustic and thermal transducers are mounted on the bottom of the pressure chamber. Electronic equipment is used for the acoustic and thermal measurements and the measurement of sample pressures and temperatures. A circulating thermal bath controls the temperature of the sediment sample and the pressure chamber.

21 Claims, 8 Drawing Figures

SUBSEAFLOOR ENVIRONMENTAL SIMULATOR

BACKGROUND OF THE INVENTION

1. Field of the Invention

The present invention relates to the measurement of ocean sediment properties, and more particularly to a subseafloor environmental simulator for measuring the sediment properties in a controlled environment.

2. Description of the Prior Art

Acoustical properties and their relationship to other physical properties of ocean sediments are important to the fields of underwater acoustics, physical oceanography and geophysics. Previously, measurements of sediment properties have been the result of in situ measurements in a real environment. These measurements have the advantage that the environment is the natural one, but there are disadvantages in that the measurements are difficult to make, the degree of disturbance is not easy to determine, and the environmental parameters are not subject to control so that one must make measurements in widely separated areas to obtain a range of parameter values. Moreover, due to limitations imposed by available measurement techniques, the in situ method can yield only limited quantities of data. Therefore, it is desired to make sediment property measurements using a controlled environment to vary parameters and to yield large quantities of useful data.

SUMMARY OF THE INVENTION

Accordingly, the present invention provides a subseafloor simulator for measuring acoustical and other physical properties of sediments at temperatures and pressures that simulate the real ocean environment. A pressure chamber has a porous piston to exert a required overburden pressure to simulate the weight of the mineral grains. An inlet port allows the fluid pressure inside the pressure chamber to be independently controlled. Acoustic and thermal transducers are mounted on the bottom of the pressure chamber. Electronic equipment is used for the acoustic and thermal measurements and the measurement of sample pressures and temperatures. A circulating thermal bath controls the temperature of the sediment sample and the pressure chamber.

Therefore, it is an object of the present invention to provide a means for simulating the real ocean environment in a controlled environment to measure the physical properties of ocean sediments.

Other objects, advantages and novel features of the present invention will be apparent from the following detailed description when read in conjunction with the appended claims and attached drawing.

DESCRIPTION OF THE PREFERRED EMBODIMENT

The two dominant properties of the ocean bottom environment to be simulated are temperature and pressure. The temperature of unconsolidated sediments in the bottom can range from near 0° at the sediment-water interface to near 100° C. at greater depths. The pressures encountered in natural sediments are frame, or overburden pressure due to the weight of the mineral grains, and pore fluid pressure resulting from the weight of the overlying water. Thus, to obtain an accurate simulated environment, temperature, frame pressure and pore pressure are controlled over the range of values encountered in the ocean bottom.

Figure 1:
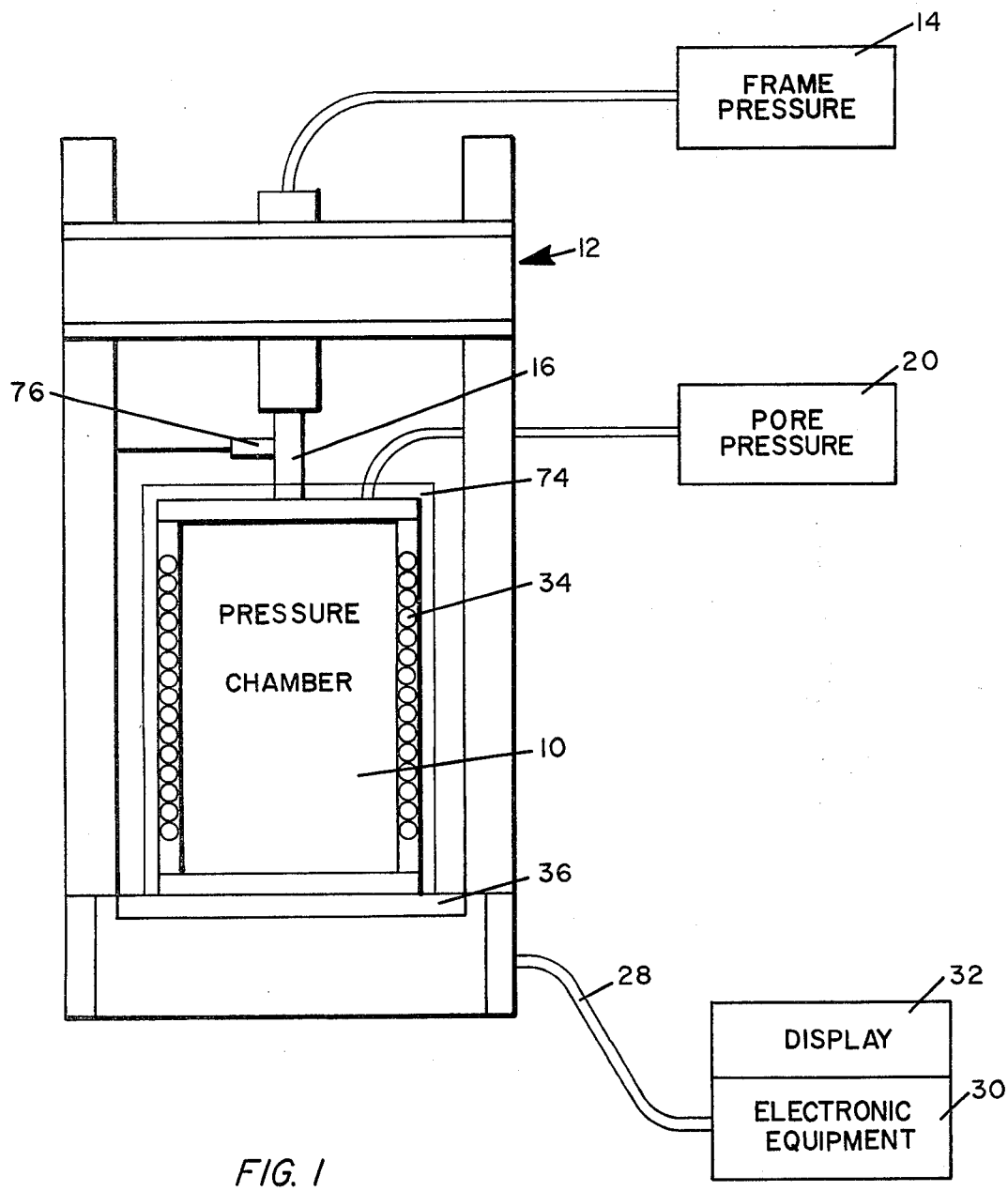
FIG. 1 is a block diagram of the subseafloor environmental simulator according the present invention.
Figure 2:
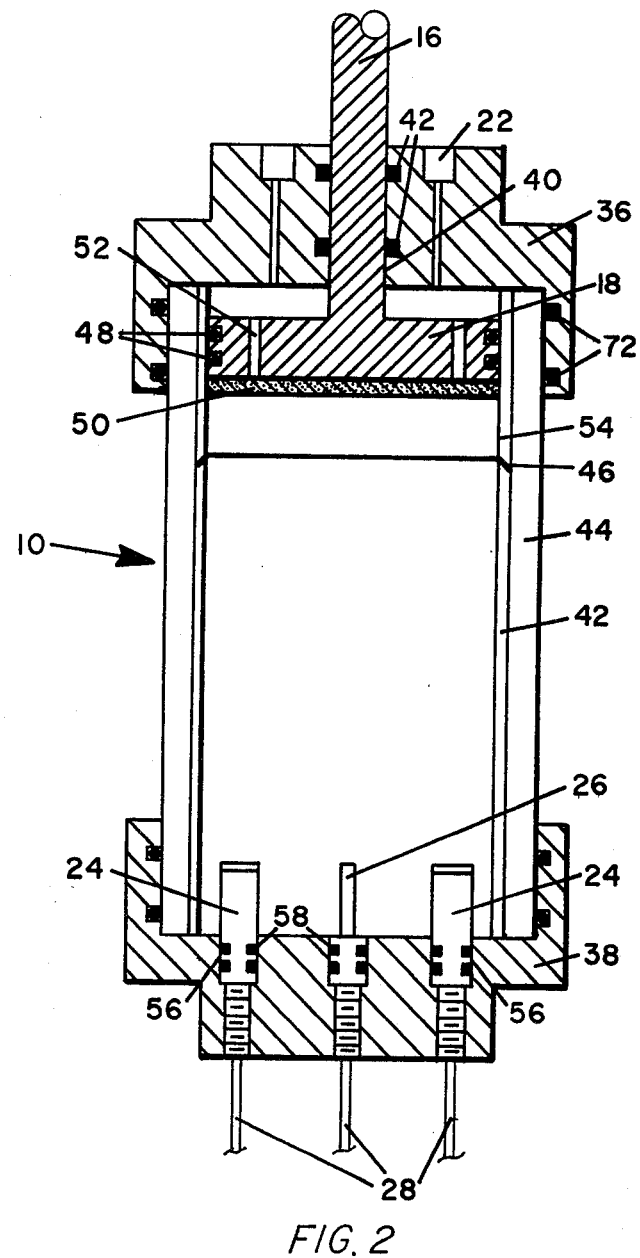
FIG. 2 is a sectional view of the pressure chamber for the subseafloor environmental simulator.

Referring now to FIGS. 1 and 2 a pressure chamber 10 is mounted in a hydraulic press 12. A first pressure pump 14 to simulate frame pressure drives a piston rod 16 having a porous piston 18 at the end internal to the chamber 10. A second pressure pump 20 supplies pore fluid pressure via an inlet port 22 in the chamber 10. Acoustic 24 and thermal 26 transducers are mounted rigidly on the bottom of the chamber 10. The transducers 24, 26 are connected by electrical cables 28 to electronic equipment 30 for the acoustic and thermal measurements. A display system 32 provides the output for the electronic equipment 30. A circulating thermal bath 34 is wrapped around the pressure chamber 10 and is bonded to it by thermally conductive epoxy. An asbestos plate 36 is placed between the bottom of the chamber 10 and the hydraulic press 12 to thermally isolate the chamber when operating far from room temperature.

The pressure chamber 10 has removable end caps 36, 38. The top end cap 36 contains a hole 40 with O-ring seals 42 to allow the piston 18 to be moved inside the chamber 10. The sediment to be tested is placed in a sleeve 42 which is placed inside a pressure case 44. The sleeve 42 has thin walls and a sharpened edge 46 to allow the sediment sample to be cut from a geophysical core and inserted inside the pressure case. The piston 18 fits closely inside the sleeve 42 and has O-ring seals 48 so that none of the sediment escapes past the piston. The face 50 of the piston 18 is covered with porous stone with drainage holes 52 through the piston behind the face to allow free movement of the pore fluid into and out of the sediment during tests. A guide ring 54 with the same thickness and diameter as the sleeve 42 is placed above the sleeve and is machined to fit over the cutting edge of the sleeve. Thus, the piston 18 starts inside the guide ring 54 and is smoothly guided into the sleeve as the sediment is compressed without damage to the piston by exposure to the sharpened edge 46. The guide ring 54/sleeve 42 combination has the same length as the pressure case 44.

The bottom end cap 38 has mounting holes 56 for the acoustic and thermal transducers 24, 26. The transducers 24, 26 are rigidly secured in the bottom end cap 38 and have O-ring seals 58 on each transducer base. Allowance is provided for three acoustic transducers 24—one projector and two receivers at different distances from the projector, and one thermal conductivity transducer in the center. Blank plugs may be inserted in the transducer holes 56 so the simulator may be used without the transducers.

Figure 3:
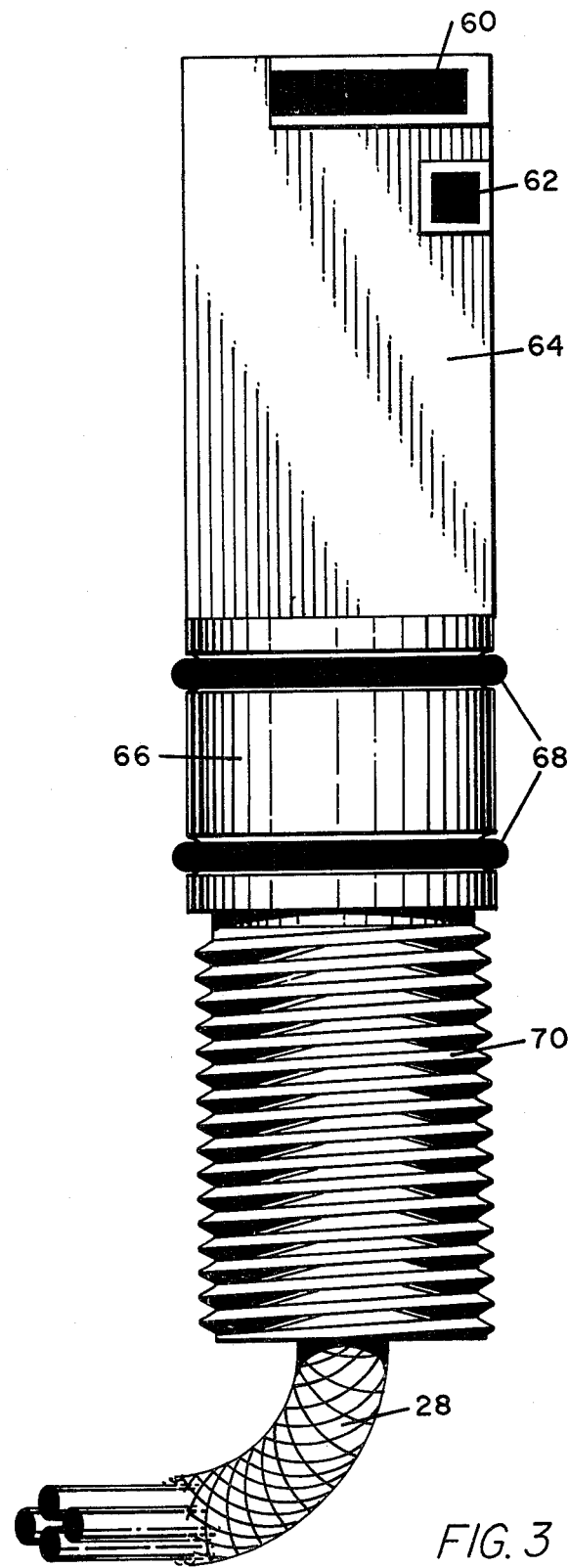
FIG. 3 is a plan view of an acoustic transducer for the subseafloor environmental simulator.

The acoustic transducer 24 is illustrated in FIG. 3. The transducer 24 has both shear wave and compressional wave elements 60, 62 mounted on a blade 64 having appropriate cutouts for the elements. The shear wave element 60 is a standard bender type element which has been used for generation and detection of shear waves in highly unconsolidated sediments. The compressional wave element 62 is a lead zirconate titanate ceramic in the form of a thin square which is polarized and driven in the thinnest direction. The shear wave element 60 is bonded to the blade 64 at the back end of the element. The compressional wave element 62 is isolated from the blade 64 but held rigidly in place by a polyurethane potting compound which covers the entire area of the blade. The blade 64 is rigidly mounted along its bottom edge to a holder 66 which has O-ring seals 68 and means such as threads 70 for being secured in the transducer hole 56. Small insulated wires are bonded in the plastic coating to connect the active elements to the shielded cable 28 which runs through the bottom of the holder 66 and connects to the electronic equipment 30. Projector and receiver transducers are identical and can be interchanged.

The thermal transducer 26 is similar to standard devices. A small thermistor bead is mounted midway inside a hypodermic needle with a fine heater wire loop which runs the length of the needle. The probe is mounted on an identical base as the acoustic transducers 24, and an identical cable 28 connects the heater wire and thermistor to the electronic equipment 30. The thermistor can be used by itself to measure the temperature of the sediment near the path of acoustical propagation, or it can be used with the heater to measure thermal conductivity.

The end caps 36, 38 have O-ring seals 72 to provide a tight seal with the pressure case 44. But the pressure inside the chamber 10 tends to force the end caps 36, 38 off, so a heavy cage 74 is used to hold the chamber together. The cage 74 secures the pressure chamber 10 to the heavy frame of the hydraulic press 12 so that the frame pressure can be exerted on the piston rod 16 projecting from the top of the chamber. Holes are provided in the bottom of the frame and the asbestos plate 36 for the cage bolt heads and the electrical cable 28.

One of the physical properties of a sediment that is of interest for comparison with acoustical properties is the porosity of the sediment. To enable calculation of the change in porosity in response to changes in frame pressure, a device 76 is provided to accurately measure the piston 18 displacement. Such a device is a linear differential transformer mounted on the hydraulic press 12 frame parallel to the piston rod 16 with the armature of the transformer connected by a clamp to the piston rod. Electronic pressure sensors 78 monitor and display the frame pressure and pore fluid pressure.

Figure 4:
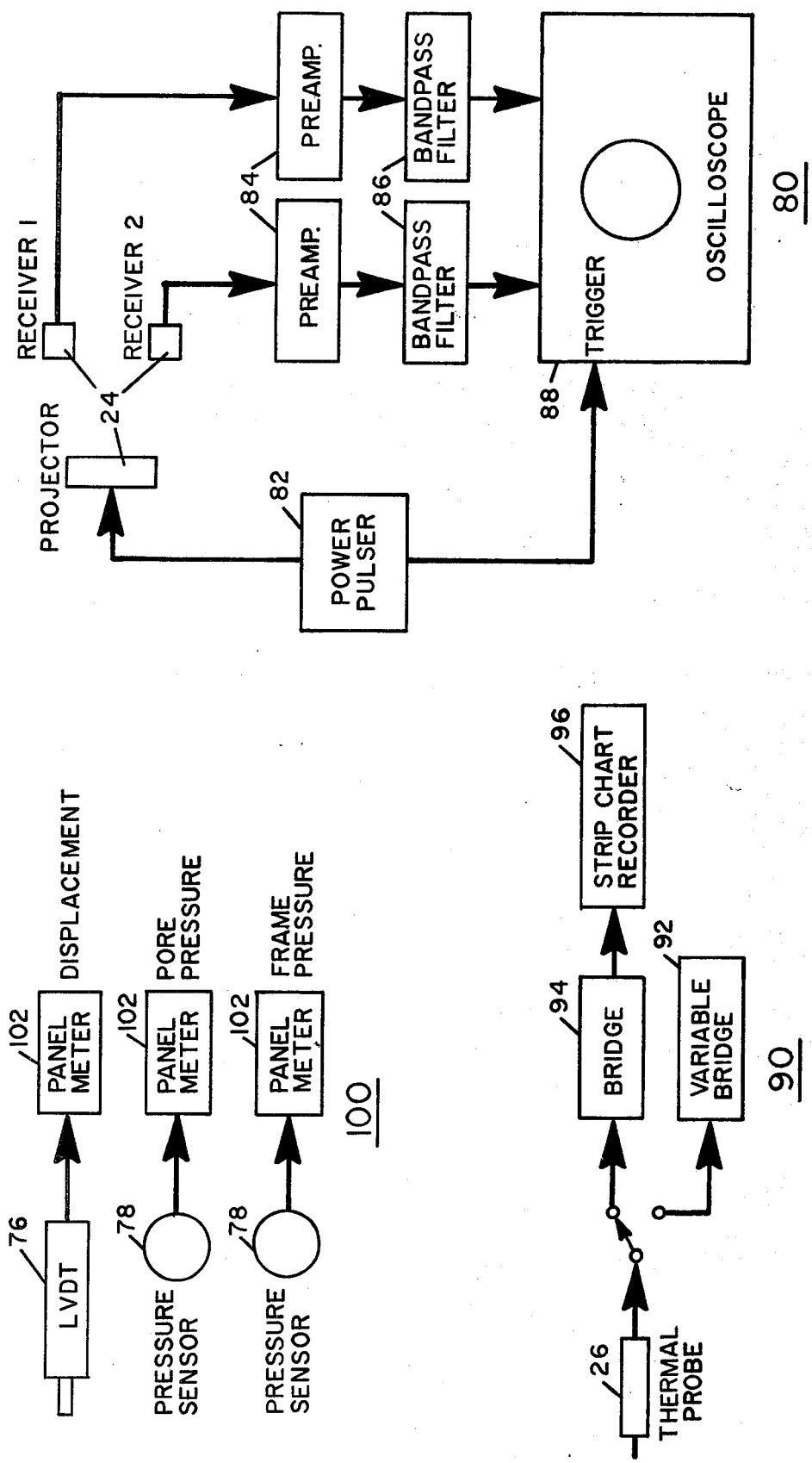
FIG. 4 is a block diagram for the electronic equipment of the subseafloor environmental simulator.

The electronic equipment as shown in FIG. 4 has three subsystems: an acoustical measurements subsystem 80, a thermal measurements subsystem 90, and a pressure and displacement measurement subsystem 100.

The acoustic subsystem 80 has a power pulse generator 82 to drive the projector transducer 24. The output of each receiver transducer 24 is passed through a preamplifier 84 and a variable bandpass filter 86. The signals are monitored on an appropriate display device such as an oscilloscope 88 from which the time difference between the received pulses can be determined.

The power pulse generator 82 drives the projecting transducer 24 with a square pulse of variable amplitude, duration and repetition rate. Typical values are: amplitude 0 to 40 volts into a 20 to 2000 ohm load; pulse duration of 1 $\mu$sec to 10 msec; and repetition rate from one pulse per ten seconds to 1000 pulses/sec. A trigger signal is provided to the display device 88 at the beginning of each transmit pulse.

The preamplifier 84 is a dual channel unit with the front end mounted on the hydraulic press 12 near the pressure chamber 10 to be near the receiver transducers 24. Thus, the high impedance cable between transducer 24 and preamplifier 84 is short to minimize noise pickup. The cable connections between the front end and main unit of the preamplifier are low impedance cables allowing long cables with minimum noise pickup and signal degradation.

Each channel of the preamplifier 84 is filtered by the bandpass filter 86 which is a readily available solid state variable filter having high and low cutoff frequencies independently variable between 10 Hz to 1 MHz, with a unity passband gain and a 24 dB per octave rolloff outside the passband.

The display device 88 has the ability to superimpose one pulse on the pulse of the other trace and the time differential, $\Delta t$, is measured and displayed digitally. The method of $\Delta t$ measurement by cycle to cycle matching in overlapped pulses is recognized as the most accurate way of sound speed measurement using pulse techniques.

The thermal measuring subsystem 90 has its input from the thermal probe 26 into one of two bridge circuits—a variable Wheatstone bridge 92 for calibration of the thermal probe and a thermal conductivity bridge 94 which allows measurement of the voltage across and the current through the resistance heater element in the thermal probe. The output of the thermal conductivity bridge 94 is recorded as a function of time on a second display device 96. Thermal conductivity is measured by recording the change of temperature, $\Delta T$, of the thermal probe 26 imbedded in the sediment sample after a known amount of electrical power is supplied to the probe heater over a period of time.

The pressure and displacement subsystem 100 supplies power to the pressure sensors 78 and the displacement device 76, the outputs of which are displayed on suitable meters 102.

Figure 5:
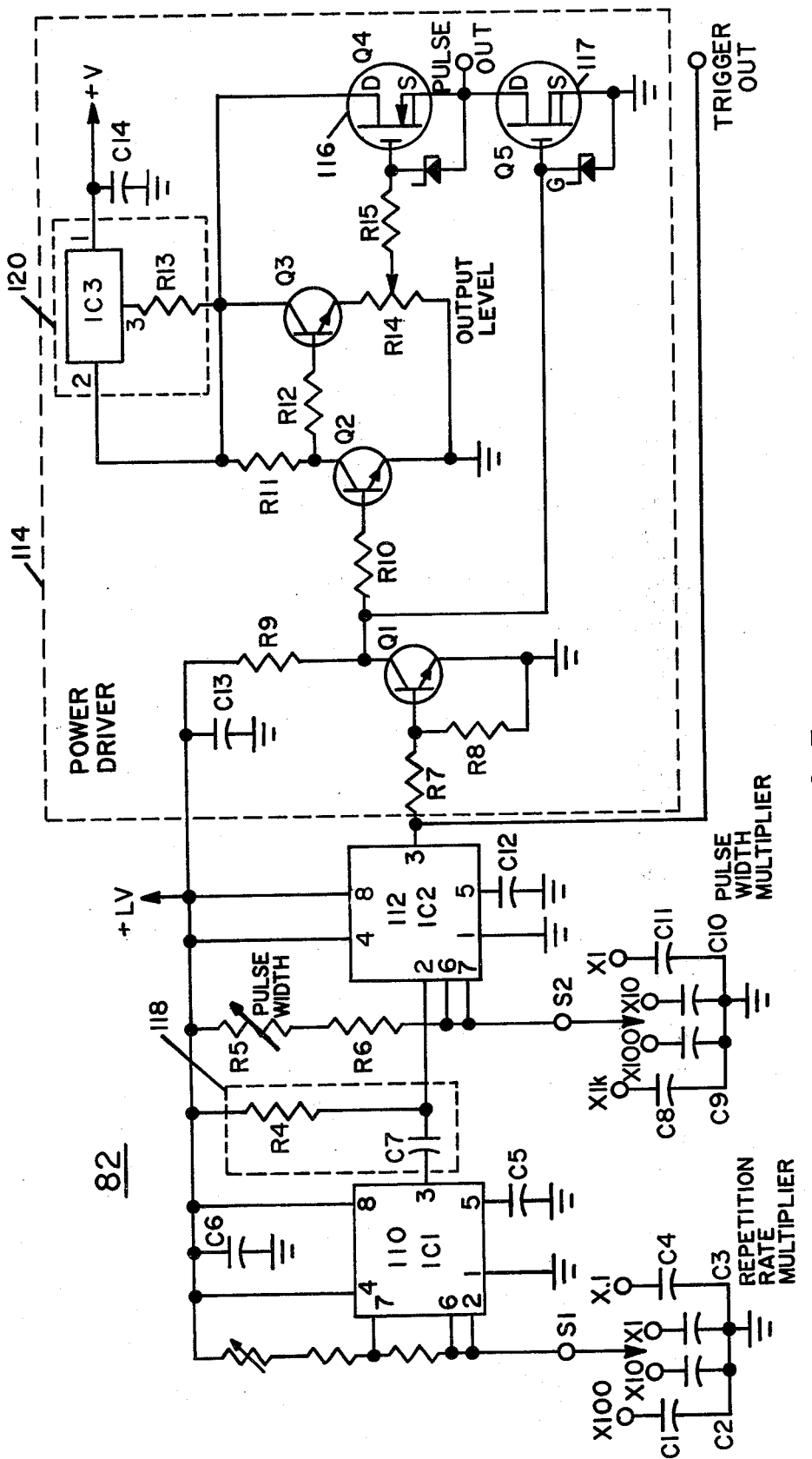
FIG. 5 is a schematic diagram for the pulse driver section for the subseafloor environmental simulator.

FIG. 5 is a schematic of the power pulse generator 82. The circuit provides two integrated circuit timers 110, 112 to provide square pulses at selected repetition rates and pulse widths to a power driver 114. The driver stage 114 uses power transistors 116, 117 to drive the projecting transducers 24. FETs are preferred for the power transistors because of their lack of secondary breakdown, their thermal stability and their near indestructibility when properly protected.

IC1 and associated components form an astable multivibrator circuit 110. The ON time of the output at pin 3 is controlled by the sum of R1, R2 and R3 and the capacitance selected by the REPETITION RATE MULTIPLIER control S1. The OFF time of the output is controlled by R3 and the selected capacitor. By properly setting R1 and S1 the ON time can be varied over the desired range of 1 msec to 10 sec, thus giving a repetition rate from 1000 pps to 0.1 pps.

The output of IC1 is coupled to the input of IC2 which together with its associated components forms a monostable multivibrator circuit 112. C7 and R4 form a differentiating network 118 to shorten the pulse applied to IC2. Each time the input of IC2 is pulsed, the output of IC2 goes ON and remains ON for a time interval determined by R5, R6 and the capacitor selected by the PULSE WIDTH MULTIPLIER control S2. By properly setting R5 and S2 the pulse width is varied over the desired range of 1 μsec to 10 msec. The output of IC2 provides the TRIGGER OUT for the display device 88.

The output of IC2 also drives the power driver 114. Q1 inverts the pulse from IC2, which pulse from Q1 drives Q2 to produce a high level pulse. The high level pulse drives emitter follower Q3 which has the OUTPUT LEVEL control R14 as the emitter resistor. The variable level pulse tapped off by R14 drives Q4, one of the power FETs connected as a source follower 116 to drive the load applied at PULSE OUT. Q5 is driven 180° out of phase to Q4 by Q1 and acts as a clamp 117 to clamp PULSE OUT to ground between pulses. Clamping of PULSE OUT reduces ringing of the projector transducer 24 and shortens the acoustic pulse generated. IC3 and R13 form a current limiter 120 for the output stage to protect the output FET 116 if PULSE OUT is shorted to ground.

Figure 6:
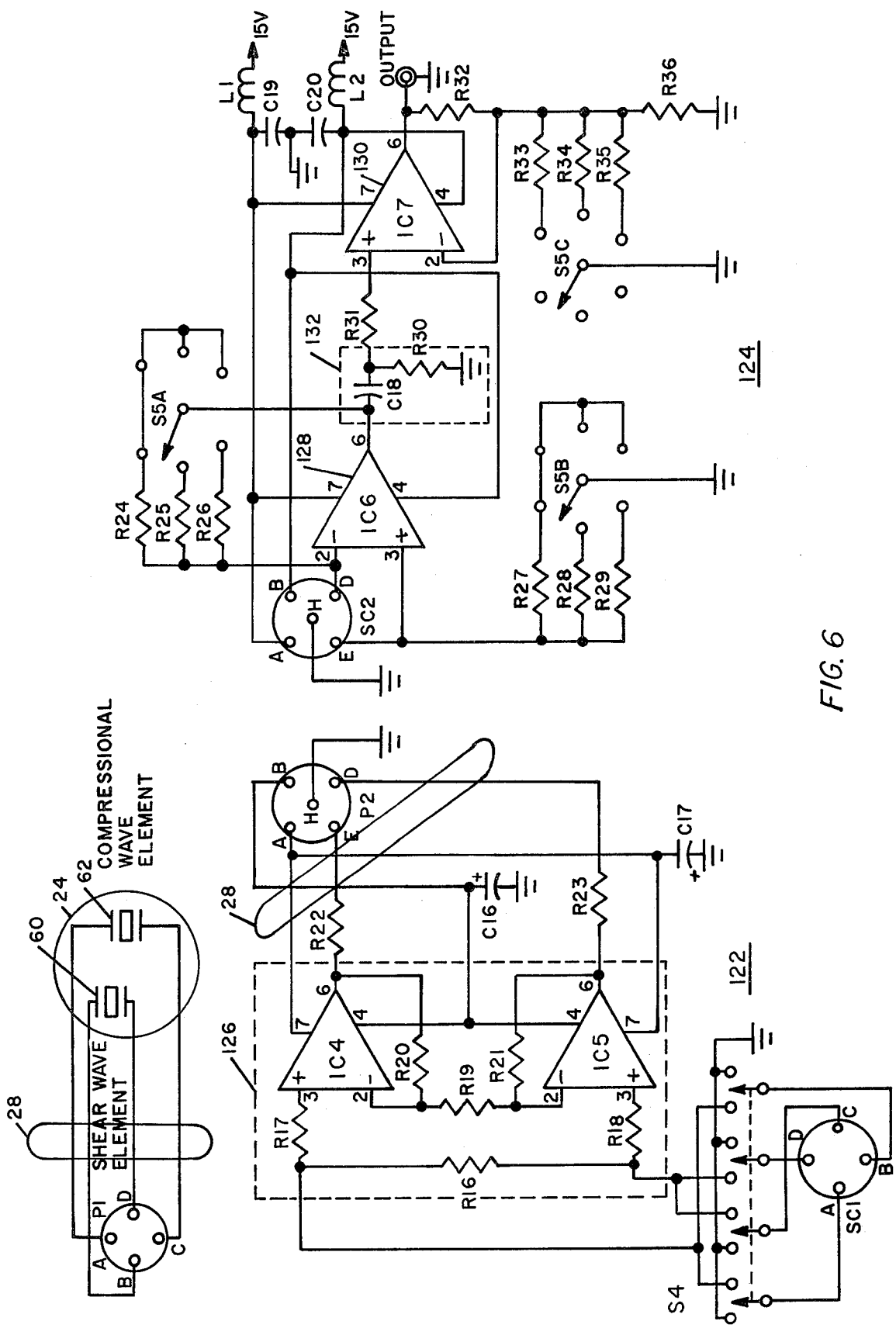
FIG. 6 is a schematic diagram for one channel of the preamplifier for the subseafloor environmental simulator.

FIG. 6 is a schematic for one channel of the preamplifier 84. Each channel is in two sections—the front end 122 housed near the transducers 24 and the main unit 124 housed with the rest of the electronic equipment 30. The shielded cable 28 connects the transducers 24 to the front end 122 through P1 and SC1, and also connects the front end to the main unit 124 through P2 and SC2. IC4 and IC5 form a differential input/differential output amplifier 126 with R19, R20 and R21 setting the gain to a desired level such as 20dB. R16 limits the input impedance to a value such as 10 MΩ. S4 selects either the shear wave element 60 or the compressional wave element 62 of the transducer 24, shorting the unused element to ground to eliminate feedover interference.

IC6 forms a variable gain differential input/single output stage 128, and IC7 is a single input/single output stage 130 with variable gain. The gain-setting resistors selected by switch S5 vary the gain of the final two stages 128, 130 over a desired range, such as 0 to 100 dB, in incremental steps such as 20 dB. Since the first stage 126 has a constant gain, the total gain of the preamplifier is variable from 20 to 120 dB for the numbers used here. C18 and R30 form an ac coupling circuit 132 so that dc offset at high gain settings does not saturate the final stage 130.

The variable bridge 92 is a standard Wheatstone bridge circuit with four decade resistor switches. The output can be monitored by a voltmeter to determine when the bridge circuit is balanced by the decade resistors. The thermistor resistance of the thermal probe 26 is then read from the decade resistors.

Figure 7:
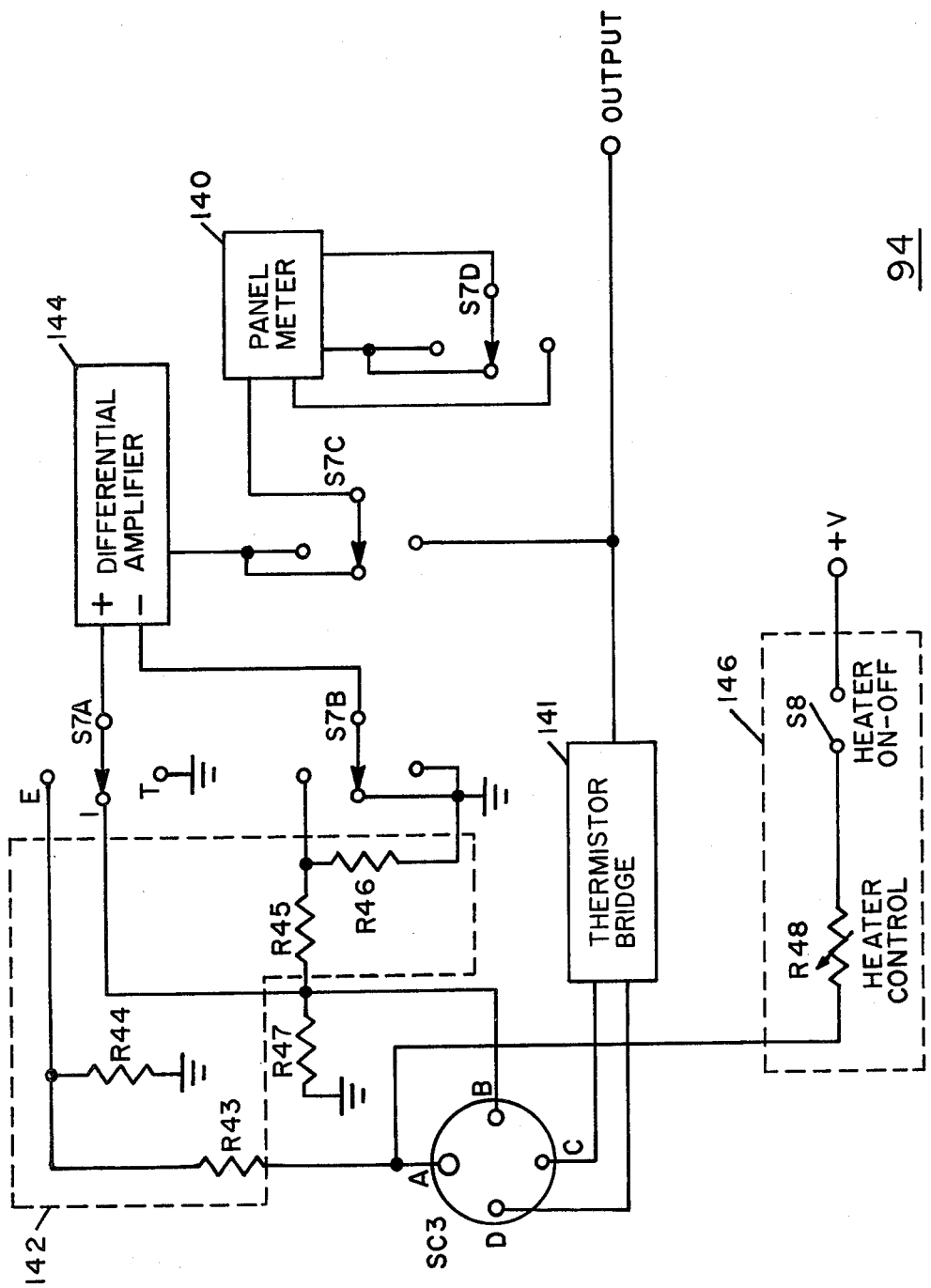
FIG. 7 is a block diagram of the thermal conductivity bridge circuit for the subseafloor environmental simulator.

FIG. 7 is a block diagram of the thermal conductivity circuit 94. SC3 is the input socket for the plug from the thermal probe 26. Pins A and B connect to the heater in the probe 26 and pins C and D connect to the thermistor. Switch S7 selects the data for display on a meter 140. In position E the meter 140 displays the voltage across the heater and in position I the heater current is displayed. In position T the temperature measured by the probe thermistor and a thermistor bridge 141 is displayed. A divide-by-ten network 142 reduces the heater voltage to the range of the meter 140. A differential amplifier 144 is a unity gain amplifier to remove the voltage offset due to R47, the current measurement resistor, from the heater voltage reading. S7D selects the meter range, and R48 and S8 form the heater control circuit 146. In the temperature mode the meter 140 displays a range R while a range switch on the thermistor bridge 141 selects $\Delta T_o$ ranges over the temperature range of interest. Thus, the actual temperature is the sum of the range switch reading, $n\Delta T_o$ and the meter reading. The output of the thermistor bridge is connected to the second display device 96 to obtain a slope of temperature versus time, a measure of thermal conductivity.

Figure 8:
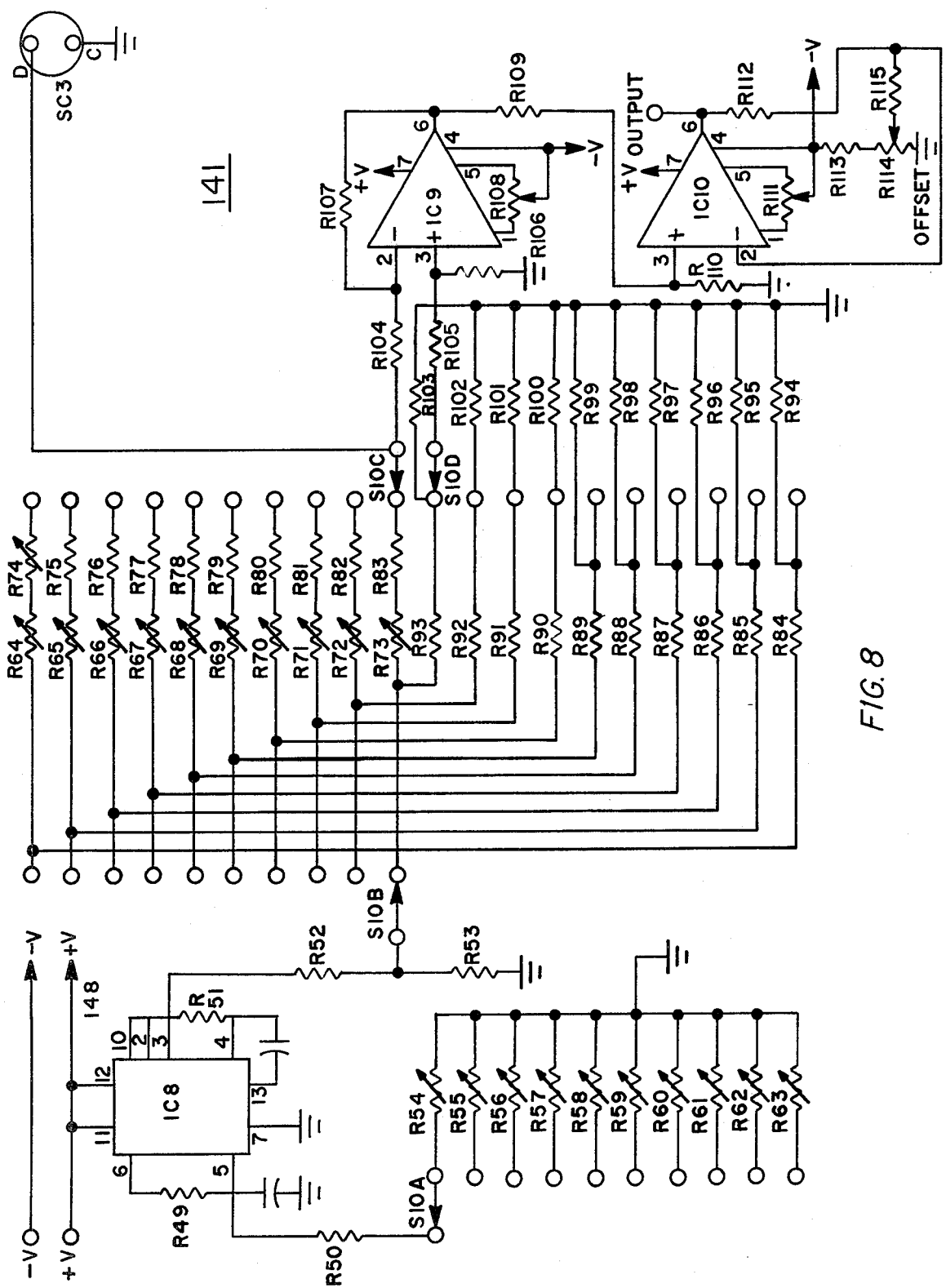
FIG. 8 is a schematic diagram for the thermistor bridge circuit of the thermal conductivity bridge circuit.

FIG. 8 is a schematic of the thermistor bridge 141. IC8 and associated elements form a low voltage regulator 148 which has a variable output selected by S10. R52 and R53 further divide the output voltage so that only a small current flows through the bridge resistors, R64 through R103, and the thermistor to reduce self-heating of the thermistor. Variable resistors R64 through R73 set the zero point of the bridge so that when the thermistor is measuring a temperature at the midpoint of a temperature range the output of IC9 can be set to zero volts. Calibration resistors R54 through R63 control the span of the bridge so that when the thermistor is measuring a temperature at the bottom end of a range the output of IC9 can be set to −5.00 volts. IC10 provides a variable offset to the output of IC9 so that the output is from 0 to 10.0 volts over a temperature range. R114 is the offset control.

The pressure and displacement display subsystem 100 provides a resistor voltage divider network to scale each voltage output so that the displays 102 read directly in pressure and displacement. Due to the differential area between the sediment piston 18 and the piston in the hydraulic cylinder of the hydraulic press 12, and because the action of the pore fluid pressure on the area of the piston rod 16 opposes the action of the frame pressure mechanism, a correction is required to obtain the correct frame pressure from the measured hydraulic pressure and is given by $$P_{frame} = a\, P_{hydraulic} - b P_{pore}$$

where a and b are constants dependent upon the respective areas of the pistons and piston rod 16.

In operation calibrations are carried out to determine acoustic transducer spacing and sensitivity, and to calibrate the thermal conductivity measuring system. Determination of transducer spacing is accomplished with distilled water in the sample chamber. Since the compressional wave speed of sound in distilled water over a large temperature range is accurately known and listed in a number of handbooks, the separation between the two receiver transducers 24 can be calculated by measuring the time differential between the two received pulses and the temperature of the water in the chamber. The separation, D, is calculated as $$D = \Delta t\, c$$

where c is the speed of sound at the measured temperature. Since the shear wave and compressional wave elements are rigidly bonded together in the transducer, the spacing determined for the compressional wave elements is assumed to be the same for the shear wave elements.

Sensitivity of the compressional wave elements are readily determined because distilled water has such a low attenuation factor that it is assumed to be zero. Thus the difference in amplitude between the received pulses from the compressional wave elements is due to spreading loss and differences in sensitivity, both of which are constant as long as the transducers are not disturbed. Thus any changes in amplitude of the received signals is interpreted as attenuation when sediment replaces the water. Since sensitivity of each element is a function of ambient temperature and does not necessarily track the response of the other element, the water calibration is made over the operational temperature range.

A rough calibration of the shear wave elements is made by measuring the received pulse amplitudes with the receiver transducers in one configuration and then with their positions switched. The medium used in this calibration is a dry sand such as Ottawa sand which generally comes to the same state of compaction if it is allowed to fall, a small amount at a time, from a height of at least one meter. The difference in amplitude of the signals from each transducer when in near and far position matches that of the other transducer and is the signal loss due to spreading and attenuation. Thus the actual sensitivity of each transducer is calculated.

For calibration of the thermal probe thermistor an accurate temperature measuring device such as a quartz thermometer or platinum resistance thermometer is used. The temperature measuring device and the temperature probe are placed together in a Lauda circulating bath so the temperature can be varied. With the probe connected to the variable bridge 92 the resistance of the thermistor is determined over the desired temperature range at closely spaced intervals, obtaining a curve of resistance versus temperature. Then a decade resistance box is connected in pins C and D of the probe socket SC3. The range switch S10 of the thermal conductivity bridge 94 is set to respective ranges with the decade resistance box set for the midpoint of the selected range. Referring to FIG. 8 the output of IC9 and the wiper of R114 are grounded while R111 is varied to produce a 0.00 volt output. The ground is removed and R114 is adjusted to produce a 5.0 volt output. Next the wipers of S10C and D are grounded and R108 is adjusted to produce a 5.0 volt output. After removing the grounds the appropriate resistor (R64 through R73) for that range is adjusted to produce a 5.0 volt output. The decade resistance box is changed to the low end of the range and the appropriate resistor (R54 through R63) is adjusted to produce 0.0 volts. The decade resistance box is then reset to midrange and appropriate resistors readjusted as necessary.

The result of the present invention is a subseafloor environmental simulator which provides the ability to determine the properties of an ocean sediment sample under controlled circumstances without the limitations inherent in in situ methodologies.

What is claimed is:

1. A subseafloor environmental simulator comprising:
   a pressure chamber to contain a sample;
   means for compressing said sample within said pressure chamber to simulate overburden pressure;
   means for allowing fluid to escape from said sample when subjected to said compressing means;
   means for applying pressure to said fluid within said pressure chamber to simulate pore fluid pressure;
   means for controlling the temperature of said pressure chamber and sample contained therein;
   means contained within said pressure chamber for measuring the acoustic and thermal conductivity properties of said sample when subjected to compression and fluid pressure at a predetermined temperature; and
   means for processing and displaying the data obtained by said measuring means.

2. A subseafloor environmental simulator as recited in claim 1 wherein said pressure chamber comprises:
   a hollow, cylindrical pressure case;
   a top end cap having an inlet port which fits securely over one end of said pressure case;
   a bottom end cap which fits securely over the other end of said pressure case; and
   a sleeve which fits snugly within said pressure case, said sleeve containing said sample.

3. A subseafloor environmental simulator as recited in claim 2 wherein said pressure chamber further comprises a guide ring which fits snugly within said pressure case, said guide ring smoothly abutting one end of said sleeve to guide said compressing means into said sleeve, said one end of said sleeve being in the form of a cutting lip.

4. A subseafloor environmental simulator as recited in claim 1 wherein said measuring means comprises:
   a thermal transducer mounted rigidly within said pressure chamber, said thermal transducer having a temperature sensing element and a heating element; and
   a plurality of acoustic transducers rigidly mounted at unequal distances from each other within said pressure chamber, each of said acoustic transducers having a compressional wave element and a shear wave element, with one of said acoustic transducers acting as a projector and the others as receivers.

5. A subseafloor environmental simulator as recited in claim 4 wherein said processing and displaying means comprises:
   an acoustical measurements subsystem to excite said projector acoustic transducer and to process and display data received from said receiver acoustic transducers to determine attenuation due to said sample;
   a thermal measurements subsystem to energize said heating element and to process and display data received from said temperature sensing element as a function of change of temperature versus time to determine thermal conductivity of said sample; and
   a pressure and displacement measurement subsystem to monitor said simulated overburden and pore fluid pressures and to monitor the amount of compaction of said sample to enable calculation of the change in porosity of said sample in response to changes in said simulated overburden pressure.

6. A subseafloor environmental simulator as recited in claim 5 wherein said acoustical measurements subsystem comprises:
   means for driving said projector transducer;
   means for separately amplifying and filtering the outputs from each of said receiver transducers; and
   means for displaying the outputs of said receiver transducers from said amplifying and filtering means as a time difference between outputs.

7. A subseafloor environmental simulator as recited in claim 6 wherein said driving means comprises:

an astable multivibrator having variable ON and OFF times to control the output repetition rate of said driving means;

a monostable multivibrator having a variable ON time to control the output pulse width of said driving means, said monostable multivibrator being triggered by the output of said astable multiplier; and a power driver connected to the output of said monostable multivibrator, said power driver having a variable level output to control the output amplitude of said driving means.

8. A subseafloor environmental simulator as recited in claim 7 wherein said driving means further comprises a differentiating circuit connecting the output of said astable multivibrator to the input of said monostable multivibrator.

9. A subseafloor environmental simulator as recited in claim 7 wherein said power driver comprises:
   an input inverter stage;
   a high level amplifier connected to the output of said input inverter stage;
   an emitter follower stage connected to the output of said high level amplifier, said emitter follower having means for varying the output level;
   a source follower connected to the output of said emitter follower to drive said projector transducer; and
   a clamping circuit connected to the output of said emitter follower to clamp the output of said source follower to ground between output pulses from said driver means.

10. A subseafloor environmental simulator as recited in claim 6 wherein said amplifying and filtering means comprises:
    a preamplifier for each of said receiver transducers, said preamplifier having a front end mounted near said receiver transducers and having a main unit, said front end having:
       a differential input/differential output amplifier to provide a fixed gain for the output of said receiver transducer, and
       means for selecting the output from either said compressional wave elements or said shear wave elements as an input;
    said main unit having:
       a variable gain differential input/single output stage,
       a single input/single output stage with variable gain,
       means for selecting the gain for said variable gain differential input/single output and said single input/single output stages in incremental steps over a desired range, and
       an ac coupling network connecting the output of said variable gain differential input/single output stage to the input of said single input/single output stage so that dc offset at high gain settings does not saturate said single input/single output stage; and
    an active bandpass filter having independently variable high and low cutoff frequencies.

11. A subseafloor environmental simulator as recited in claim 5 wherein said thermal measurements subsystem comprises:
    means for calibrating said thermal probe;
    a thermal conductivity circuit to provide electrical energy to said heating element and to process the output data of said thermal probe; and
    means for recording the change of temperature detected by said temperature sensing element as a function of time when said heating element is conducting.

12. A subseafloor environmental simulator as recited in claim 11 wherein said thermal conductivity circuit comprises:
    means for providing said electrical energy to said heating element, said providing means being variable;
    means for measuring the voltage and current of said heating element;
    a differential amplifier to remove dc offset due to said current measuring means; and
    a thermistor bridge connected to the output of said temperature sensing element, said thermistor bridge having a plurality of switchable discrete ranges within the temperature range of interest.

13. A subseafloor environmental simulator as recited in claim 12 wherein said thermistor bridge comprises:
    a low voltage regulator having a variable output;
    means for limiting the current through said temperature sensing element to a small value to reduce self-heating of said temperature sensing element;
    means for setting the zero point of said thermistor bridge at the midpoint of said switchable discrete ranges; and
    means for controlling the span of said thermistor bridge for each of said switchable discrete ranges.

14. A subseafloor environmental simulator as recited in claim 1 wherein said compressing means comprises:
    a hydraulic press within which said pressure chamber is placed; and
    means for transferring the pressure exerted by said hydraulic press to said sample within said pressure chamber.

15. A subseafloor environmental simulator as recited in claim 14 wherein said transferring means comprises:
    a piston containing within said pressure chamber, said piston fitting snugly within said pressure chamber; and
    means for connecting said piston to said hydraulic press so that when said hydraulic press exerts pressure said piston is moved to compress said sample within said pressure chamber.

16. A subseafloor environmental simulator as recited in claim 15 wherein said allowing means comprises a porous face on said piston, said piston having drainage holes behind said face to allow said fluid to flow behind said piston when said sample is compressed.

17. A subseafloor environmental simulator as recited in claim 1 wherein said controlling means comprises:
    a copper coil wrapped around said pressure chamber, said copper coil being in close thermal contact with said pressure chamber; and
    a thermal bath circulating through said copper coil to transmit heat to said pressure chamber and said sample contained therein.

18. A subseafloor environmental simulator as recited in claim 1 further comprising means for securing said pressure chamber within said hydraulic press to prevent said top and bottom end caps from being forced off the ends of said pressure case when said sample and fluid is subjected to said simulated pressures.

19. A subseafloor environmental simulator as recited in claim 18 wherein said securing means comprises a cage which fits over said pressure chamber, said cage being securely fastened to the bottom of said hydraulic press.

20. A subseafloor environmental simulator as recited in claim 1 further comprising means for thermally isolating said pressure chamber from said hydraulic press.

21. A subseafloor environmental simulator as recited in claim 20 wherein said thermally isolating means comprises a pad of thermally insulative material placed between said bottom end cap and said hydraulic press.

* * * * *